United States Patent [19]

Larner et al.

[11] Patent Number: 5,122,603
[45] Date of Patent: Jun. 16, 1992

[54] PURIFIED INSULIN MEDIATORS AND PURIFICATION PROCESS FOR SAME

[75] Inventors: Joseph Larner; Alison Kennington; Laura Huang; Tsung Y. Shen, all of Charlottesville, Va.

[73] Assignee: The University of Virginia Alumni Patents Foundation, Charlottesville, Va.

[21] Appl. No.: 320,484

[22] Filed: Mar. 8, 1989
(Under 37 CFR 1.47)

[51] Int. Cl.$^5$ .................... C07K 15/00; C07G 7/00; C12N 9/88; A01N 57/00
[52] U.S. Cl. .................... 536/18.7; 536/119; 514/103; 514/866; 514/573; 514/23; 530/395; 530/397; 435/232; 436/161; 436/162
[58] Field of Search ............ 536/119, 18.7; 514/103, 514/23, 866, 573; 260/112; 530/344, 841; 435/184, 232; 436/161, 162

[56] References Cited

U.S. PATENT DOCUMENTS

| | | | |
|---|---|---|---|
| 4,446,064 | 5/1984 | Larner et al. | 530/841 |
| 4,839,466 | 6/1989 | Saltiel | 536/18.7 |
| 4,921,877 | 5/1990 | Cashmere et al. | 514/866 |
| 4,952,568 | 12/1990 | Sawai et al. | 514/866 |
| 4,954,448 | 9/1990 | Wiegand et al. | 435/184 |
| 5,023,248 | 6/1991 | Siren | 514/573 |

OTHER PUBLICATIONS

Thakkar, et al.; Journal Biol Chem; (4-1990); 265(10) pp. 5475-5481.
Niwa, et al; Journal Chromatography; (10-83); 277 pp. 25-39.
Mato, et al; Journal of Biological Chemistry; (262) pp. 2131-2137 (1987).

Primary Examiner—Ronald W. Griffin
Assistant Examiner—Louise Leary
Attorney, Agent, or Firm—Oblon, Spivak, McClelland, Maier & Neustadt

[57] ABSTRACT

A method for purifying two distinct insulin mediators to substantial homogeneity, and relative purity values above 80%, comprises adsorption on first anion exchange resin and subsequently on a chelex cation exchange resin column. The chelex resin ion exchange column substantially increases the activity of the recovered mediator. Following purification, the already treated fraction is subjected to three successive thin layer chromatography purification steps, the last giving, in the presence of ninhydrin stain, a characteristic salmon-color spot, which is indicative of the presence of the mediator. This process can also be used as a screening process, the absence of the salmon-colored spot being indicative of the diabetic state. Structure information on the insulin mediators obtained is given.

7 Claims, No Drawings

PURIFIED INSULIN MEDIATORS AND PURIFICATION PROCESS FOR SAME

BACKGROUND OF THE INVENTION

1. Field of the Invention

This invention pertains to naturally-occurring insulin mediators, and in particular, two purified insulin mediators obtained from liver tissue. Additionally, a process for purification of the naturally-occurring substances is provided, together with a screening test for the detection of the diabetic state. Related artificial compounds can be similarly prepared

2. Background of the Prior Art

Numerous researchers have established that insulin, a major anabolic hormone, which plays a central role in the control of metabolism of carbohydrates, fats and proteins, acts indirectly, through the activity of a plurality of insulin mediators, that apparently link the hormone, and a variety of regulating enzymes. Thus, Larner, *Diabetes*, 21, page 428 (1972) suggested the existence of an insulin mediator blocking the activation of cyclic AMP-dependent protein kinase Subsequently, Jarett et al, *Science* 206, pages 1407-1408 (1979) confirmed the activation, by the proposed mediators, of PDH in adipocyte mitochondria. Subsequently, Mato et al, *Journal of Biological Chemistry* 262, pages 2131-2137 (1987), and Saltiel et al, *Proceedings of the National Academy of Science* 83, pages 5793-5797 (1986) have identified insulin "modulators", similar to glycosyl-phosphoinositol linkers known to anchor proteins to the external surface of cell membranes.

Thus, substantial evidence has been provided that there exists a plurality of insulin mediators which operate in conjunction with specific enzymes, in the multiple functions of insulin. There are at least suggestions that one or more of these mediators is derived from traditional glycosyl-phosphoinositol linkers, similar to known anchor proteins.

Effective identification and treatment of the diabetic state, and other functions controlled or impacted by insulin, may be most effectively carried out through the mechanism of insulin mediators. U.S. Pat. No. 4,446,064, Larner et al, discloses a partial purification process for the isolation of an insulin mediator substance derived from muscle tissue, the isolated fraction having the ability to inhibit protein kinase However, the purification system provided therein is incomplete, and the structure of the mediator collected in the obtained fraction is not identified. Effective in vivo treatment of diabetes, and related insulin conditions, as well as the use of the mediators as diagnostics, requires high degrees of purification of mediator substances. Additionally, production of large amounts of the mediator substance, preferably through synthetic or biological means, requires identification of structure information concerning these mediators.

Accordingly, it remains an objective of the art to provide a highly purified insulin mediator, a system for purification of the same, and the structure of the insulin mediator, for the more effective treatment of insulin-resistant conditions.

SUMMARY OF THE INVENTION

At least two insulin mediator substances have been obtained in highly purified form from the liver of mammals, including rats, bovines and swine. The organism can either be directly injected with insulin, or the liver tissue collected therefrom be exposed to insulin, after homogenization of the liver tissue, to obtain the membranes thereof The collected liver tissue is treated with acid, if the liver tissue membrane is exposed to insulin, to stop the incubation, and both types of liver tissue are subsequently boiled to denature the proteins present Denatured protein is removed by centrifugation and the remaining supernatant is purified by charcoal adsorption, to remove nucleotides, such as ATP, ADP and AMP. The deproteinized, charcoal-purified material is adsorbed onto an anion exchange resin, and eluted with dilute HCl. Two separate fractions are obtained, the first at a pH of 2.0, and the second at a pH of 1.3-1.5.

The separate fractions are subsequently introduced to sizing columns. The pH 2.0 fraction is exposed to a sizing column such as P4, while the pH 1.3-1.5 fraction is run through a G10 or similar, sizing column. Such sizing columns are conventionally used to remove inorganic salts, and their use is the same herein. The fractions collected are lyophilized, and redissolved in minimal volumes of water. The pH 2.0 fraction, is activated by adsorption onto a cation exchange resin column, such as a chelex resin column. The fraction is eluted with 1 N HCl. The chelex column appears to activate this fraction, giving an increase observed in the activation of pyruvate dehydrogenase, in vitro studies, of about 5-fold.

The eluted material is again chromatographed on sizing columns, and after recovered from the sizing columns, subjected to three successive thin layer chromatography purification steps (TLC 1-3). TLC 1 employs a solvent system of n-propanol and water, TLC 2 employs a solvent system of ethylene glycol monoethylether, propionic acid, water, and TLC 3 employs a quaternary system, isopropanol, pyridine, acidic acid and water.

The fraction recovered from the TLC solvent systems is passed through a sizing column, the fraction recovered, after removal of insolubles, being essentially homogeneous. The relative purity of the recovered fractions is well above 80%, and may be as high as 90%, or better.

TLC 3 can also be used as a an analytical tool to confirm the presence of the mediator Presence of the mediator in the isolated fraction in TLC 3 gives a characteristic salmon-colored spot when the plate is treated with ninhydrin stain, quite distinct from the characteristic purple color normally produced.

Various synthetic analogues of the natural materials may be based on characteristics of the natural material structures, to reduce synthesis obstacles.

DETAILED DESCRIPTION OF THE INVENTION

The insulin mediator fractions that are the focus of this invention are derived from liver tissue While it is believed that similar mediator substances are found in other tissue systems, the mediators are collected in the greatest quantity from the liver material of mammals, and accordingly, prior to a synthetic or biological production system, this is the best source for recovery.

The mammalian liver source may be exposed to insulin either by direct injection of the mammal, or by exposure of the liver membrane tissue to insulin, in vitro. As an example, rats were injected with insulin (5 U/kg) via the tail vein. The rats are sacrificed after five minutes, with the livers being removed immediately and frozen in liquid nitrogen Alternatively, the liver tissue is homogenized and the membranes obtained by centrifugation. Membrane collected is incubated together with insulin (1 mu/ml in a pH 7.4 buffer system further containing ATP, Mn$^{2+}$, BSA, PMSF and aprotonin). The incubation is terminated by the addition of formic acid, or similar acid, to a pH of 3.5. The material obtained through either method is boiled, so as to denature existing proteins The denatured proteins can be removed by gross filtration methods, or centrifugation. The recovered material is further purified by adsorption onto charcoal, to remove major nucleotides such ATP, ADP and AMP.

The resulting material, from which major protein and nucleotide fractions have been removed, is adsorbed onto an anion exchange resin and eluted One exemplary resin is an AG1X8 resin, although other anion exchange resins may be used, with similar results. The mediators are eluted with dilute HCl. Two separate fractions are eluted, the first at a pH of about 2.0, the second at a pH of about 1.3–1.5. In general, both fractions will receive similar subsequent processing. However, because of the different nature of the two fractions, different sizing columns will generally be used. Unless indicated to the contrary, it should be understood that both fractions are subjected to the same purification procedure.

The recovered, eluted pH 2.0 fraction is adsorbed onto a cation exchange resin, such as a chelex resin. Elution therefrom with 1 N HCl gives a sharp increase in PDH-activating activity observed in vitro, on the order of a 5-fold increase. It should be noted that the use of a cation exchange resin, such as the chelex resin, is essential to achieve this marked increase in activation. Such resins are conventionally used for the removal of trace amounts of heavy metals.

Both fractions are purified to essential homogeneity through thin layer chromatography, after repeated lyophilization and sizing, as necessary. In general, the pH 2.0 fraction and the pH 1.3–1.5 fraction can be purified on a sizing column such as P4 sizing column.

The recovered material is subjected to repeated thin layer chromatography. Although other formats may be used, silica plates were found to be most efficacious, the active material being recovered after each TLC phase by scraping, elution with distilled water, or HCl of appropriate pH, and repeated lyophilization. In TLC 1, a solvent system of n-propanol: water of 7:3 is employed. The eluted material is then subjected to TLC 2 using a ternary system of ethylene glycol monoethylether: propionic acid: water of proportions 70:15:15. Subsequently, in TLC 3, the remaining material is purified in a quaternary system, employing isopropanol: pyridine: acetic acid: water in proportions 8:8:1:4.

The resulting material is essentially pure, with TLC impurities remaining. These are removed through further sizing, and high performance liquid chromatography, employing typical HPLC columns, such as a GLYCO-PAK or BONDAPAK C18 HPLC column. Most effective purification can be achieved using a minimal volume of 0.1% TFA with elution of the material using the same substance, or a water equilibrated P2 column. Beef or pork liver can also be used to prepare mediator by similar methods.

It should be noted that the mediator, if present, gives a unique and easily recognized signature in the TLC 3 solvent system, upon application of a ninhydrin stain. The salmon-color spot obtained is easily and quickly recognized. This qualitative recognition step offers an effective analytical tool, as well as a purification medium. Thus, one practicing the purification system described above, can quite quickly screen a donor substance so purified for the presence of the mediators. Absence of the mediator may be indicative of the diabetic state. Thus, as applied to mammals, including humans, a tissue sample taken, and treated with the above purification system through the TLC 3 step, can be quickly screened. Absence of the characteristic of the salmon-colored spot suggests the individual should be further tested, for confirmation of the diabetic indication As this would be a screening process only, those of skill in the art will recognize that the activation treatment on the cation exchange resin, such as a chelex resin, described above, can be dispensed with, as this is essentially an activation step.

Material treated according to the above process has analyzed for structure, by gas chromatography/mass spectroscopy, and associated analytic techniques. GC analysis indicates the presence of mannose, D-chiroinositol and galactosamine in the pH 2.0 mediator. Additional analysis indicates the mediator to be an anchor-type protein of the approximate structure represented below:

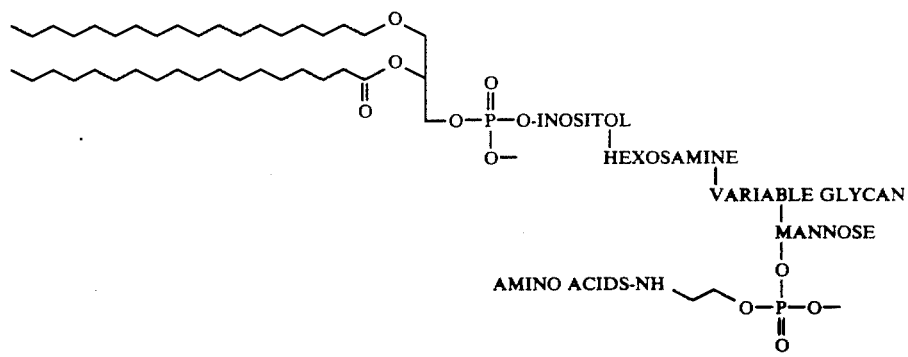

It is presumed that, when intact, the fatty acid terminal portion is linked to the cell membrane of the organism. Certainly, such phosphate linkage opportunities occur in virtually all mammalian cell membranes, and accordingly, the active unit is believed to begin with the inositol grouping Further analysis has confirmed the structure of the mediator fractions as follows.

The pH 2.0 fraction, having the biological property of activating pyruvate dehydrogenase for the formation of acetyl-CoA from glucose, has been analyzed as having a chiroinositolhexosamine disaccacharide, linked to the glycol fatty acid through a phosphoester linkage. An additional carbohydrate moiety, probably comprised of 1-3 mannose units are linked through a phosphoester-ethanolamine bond to an amino acid linkage to a protein, in vivo.

While reproduction of the entire structure will of course give a biologically active compound, extended carbohydrate synthesis is difficult. Biologically active compounds would include synthetic compounds capable of activating pyruvate dehydrogenase in vivo. Typically, these comprise the disaccharide component D-chiroinositol/hexosamine together with extender units, typically by hydrocarbon units, terminating in a hydroxyl group for the phosphoester linkage.

Similarly, the pH 1.3-1.5 mediator has the characteristic biological activities of inhibiting both a cAMP kinase and adenylate cyclase. Analysis shows this mediator to have a myoinositol/hexosamine disaccharide, followed by 3 mannose units bearing galactose side chains. Again, a synthetic substitute would have at least one of these biological activities. Such analogues include the myoinositol/hexosamine disaccharide and 1-3 mannose units, with appropriate linkage units Again hydrocarbon extenders may be used in place of carbohydrate units if necessary. Work is currently underway to determine whether or not addition of vanadate or diacyglycerol compounds to the mediator can achieve glucose transport characteristics, to duplicate the effects of insulin. When resolved, such studies should result in improved pharmaceuticals for the treatment of diabetes The mediators, as purified, offer a tremendous resource in the screening and diagnosing of the diabetic state, as well as materials for the preparation of insulin-like pharmaceuticals for the treatment of specific conditions associated with diabetes.

The invention addressed herein has been described both generally and by example above. Those of skill in the art will recognize that the exemplary recitations are not intended to limit the invention, and that substitution and derivation can be practiced, without departing from the scope of the invention. In particular, heat and time parameters, as well the identity of various resins used for purification, can be altered, without inventive effort. Such substitutions do not depart from the scope of the invention. It is therefore to be understood that within the scope of the appended claims, the invention may be practiced otherwise than as specifically described herein.

What is claimed is:

1. A process for the purification of at least one insulin mediator to essential homogeneity, comprising:
   exposing the liver cell membranes of a mammal to insulin, recovering the so-exposed liver material and purifying said mediator according to the following purification scheme comprising the sequential steps of:
   1) boiling the collected liver cell membrane sample to denature proteins present therein, and removing said denatured proteins,
   2) adsorbing the sample onto charcoal, to remove major nucleotides, and eluting the fraction therefrom,
   3) adsorbing the sample onto an anion exchange resin column and eluting the sample therefrom to obtain two separate fractions by eluting with dilute HCl, the first fraction being eluted at pH 2.0 and the second fraction being eluted at pH 1.3-1.5, and further processing at least one said fraction as follows,
   4) adsorbing said pH 2.0 fraction onto a cation exchange chelex resin, and eluting the adsorbed sample with 1N HCl,
   5) passing said separate fractions through separate sizing columns to remove impurities introduced through steps 1-4,
   6) subjecting the fraction recovered from said sizing columns to three successive thin layer chromatography purification steps, each said thin layer chromatography step comprising a distinct solvent system, first employing n-propanol: water in a ratio of 7:3, the second comprising ethylene glycol monoethylether propionic acid: water in a ratio of 70:15:15 and the third comprising isopropanol: pyridine: acidic acid: water in a ratio of 8:8:1:4,
   7) removing impurities introduced through said thin layer chromatography steps, whereby a sample of insulin mediator of substantial homogeneity, and relative purity above 80% is recovered.

2. The process of claim 1, wherein the pH 2.0 fraction is purified on a sizing column distinct from that employed in the purification of the pH 1.3-1.5 fraction.

3. The relatively pure insulin mediator preparation obtained by the process of claim 1, when only said pH 2.0 fraction is purified.

4. The relatively pure insulin mediator preparation obtained by the process of claim 1, when only said pH 1.3-1.5 fraction is purified.

5. A relatively pure preparation having the biological activity of activating pyruvate dehydrogenase, and comprising a D-chiroinositol/hexosamine disaccharide.

6. A relatively pure preparation having at least one of the biological activities of inhibition of cAMP kinase or inhibition of adenylate cyclase, and comprising a myoinositol/hexosamine disaccharide.

7. A method for screening mammals for the presence of an insulin mediator, which may be indicative of the diabetic state, comprising:
   obtaining a liver tissue sample from said mammal,
   purifying said sample to remove proteins and nucleotides therefrom by boiling, followed by charcoal adsorption,
   adsorption of the purified fraction on an ion exchange resin,
   eluting said adsorbed fraction with HCl at a pH of 2.0, and pH 1.3-1.5, purifying said recovered eluants on a sizing column,
   subjecting said fractions to three subsequent thin layer chromatography steps, the first employing a solvent system of n-propanol: water of 7:3 proportions, the second employing a solvent system comprising ethylene glycol monoethylether: propionic acid: water in proportions of 70:15:15 and the third employing a solvent system comprising isopropanol: pyridine acidic acid water in a proportion of 8:8:1:4,
   applying ninhydrin stain to the plate on which said third thin layer chromatography purification step is practiced, wherein the absence of a salmon-colored fraction on said stained plated is indicative of the diabetic state in said mammal.

* * * * *